US012725698B2

(12) United States Patent
Luo et al.

(10) Patent No.: US 12,725,698 B2
(45) Date of Patent: Sep. 1, 2026

(54) INFORMATION PROCESSING DEVICE, INFORMATION PROCESSING METHOD, AND RECORDING MEDIUM

(71) Applicant: NEC Corporation, Tokyo (JP)

(72) Inventors: Yuan Luo, Tokyo (JP); Kosuke Nishihara, Tokyo (JP)

(73) Assignee: NEC CORPORATION, Tokyo (JP)

( * ) Notice: Subject to any disclaimer, the term of this patent is extended or adjusted under 35 U.S.C. 154(b) by 75 days.

(21) Appl. No.: 18/728,560

(22) PCT Filed: Jan. 28, 2022

(86) PCT No.: PCT/JP2022/003335
§ 371 (c)(1),
(2) Date: Jul. 12, 2024

(87) PCT Pub. No.: WO2023/145001
PCT Pub. Date: Aug. 3, 2023

(65) Prior Publication Data
US 2025/0095831 A1 Mar. 20, 2025

(51) Int. Cl.
*G16H 40/20* (2018.01)
*G16H 10/60* (2018.01)

(52) U.S. Cl.
CPC ............. *G16H 40/20* (2018.01); *G16H 10/60* (2018.01)

(58) Field of Classification Search
CPC .............................. G16H 40/20; G16H 10/60
See application file for complete search history.

(56) References Cited

U.S. PATENT DOCUMENTS 11,361,386 B2 * 6/2022 Phillips .................. G16H 10/60
11,574,729 B1 * 2/2023 Ventura .................. G16H 40/20
2023/0105348 A1 * 4/2023 Vodencarevic ........ G16H 10/60 705/2

FOREIGN PATENT DOCUMENTS

JP 2012-142028 A 7/2012
JP 2019-101675 A 6/2019
JP 6908952 B1 7/2021

OTHER PUBLICATIONS

International Search Report for PCT Application No. PCT/JP2022/003335, mailed on Apr. 12, 2022.

(Continued)

*Primary Examiner* — Michael I Ezewoko
(74) *Attorney, Agent, or Firm* — Sughrue Mion, PLLC

(57) ABSTRACT

In an information processing device, a sickbed information acquisition means acquires sickbed information concerning use states of sickbeds in each hospital. A patient information acquisition means acquires patient information concerning patients of hospitals. A facility information acquisition means acquires facility information concerning use states of facilities of each hospital. A shift information acquisition means acquires shift information concerning a work shift of medical professionals working at the hospitals. A sickbed availability prediction means predicts availability states of the sickbeds based on the sickbed information and the patient information. An unacceptable patient prediction means predicts unacceptable patients whom each hospital cannot accept, based on the patient information, the facility information, and the shift information. An acceptable patient information generation means generates acceptable patient information concerning acceptable patients whom the hospitals can accept, based on the availability states of the sickbeds and the unacceptable patients which are predicted.

8 Claims, 10 Drawing Sheets

SHIFT INFORMATION

| STAFF ID | JOB TITLE | RESPONDABLE SEVERITY (1 to 3) | WORKING DATA |
|---|---|---|---|
| D01 | PHYSICIAN (RESPIRATORY) | 3 | WORKING DATA D01 |
| D02 | PHYSICIAN (GASTROENTEROLOGY) | 3 | WORKING DATA D02 |
| ⋮ | ⋮ | ⋮ | ⋮ |
| E01 | NURSE | 3 | WORKING DATA E01 |
| E02 | NURSE | 2 | WORKING DATA E02 |
| ⋮ | ⋮ | ⋮ | ⋮ |

| Sun | Mon | Tue | Wed | Thu | Fri | Sat |
|---|---|---|---|---|---|---|
| 1 X | 2 X | 3 X | 4 X | 5 X | 6 X | 7 X |
| 8 X | 9 X | 10 3 pts | 11 1 pt | 12 2 pts | 13 X | 14 X |
| 15 X | 16 3 pts | 17 2 pts | 18 2 pts | 19 X | 20 2 pts | 21 3 pts |
| 22 3 pts | 23 1 pt | 24 X | 25 3 pts | 26 X | 27 1 pt | 28 3 pts |
| 29 X | 30 1 pt | 31 X | | | | |

(56) References Cited

OTHER PUBLICATIONS

Miyaoka et al., "Medical IT system realized by FileMaker_Build a 'Bed Control System' that supports appropriate bed management and team medical care by displaying information on bed occupancy rates and transitions of entering and leaving a hospital", 1st Medical IT Expo, Sep. 12, 2018, pp. 10-11.

* cited by examiner

Figure 1:
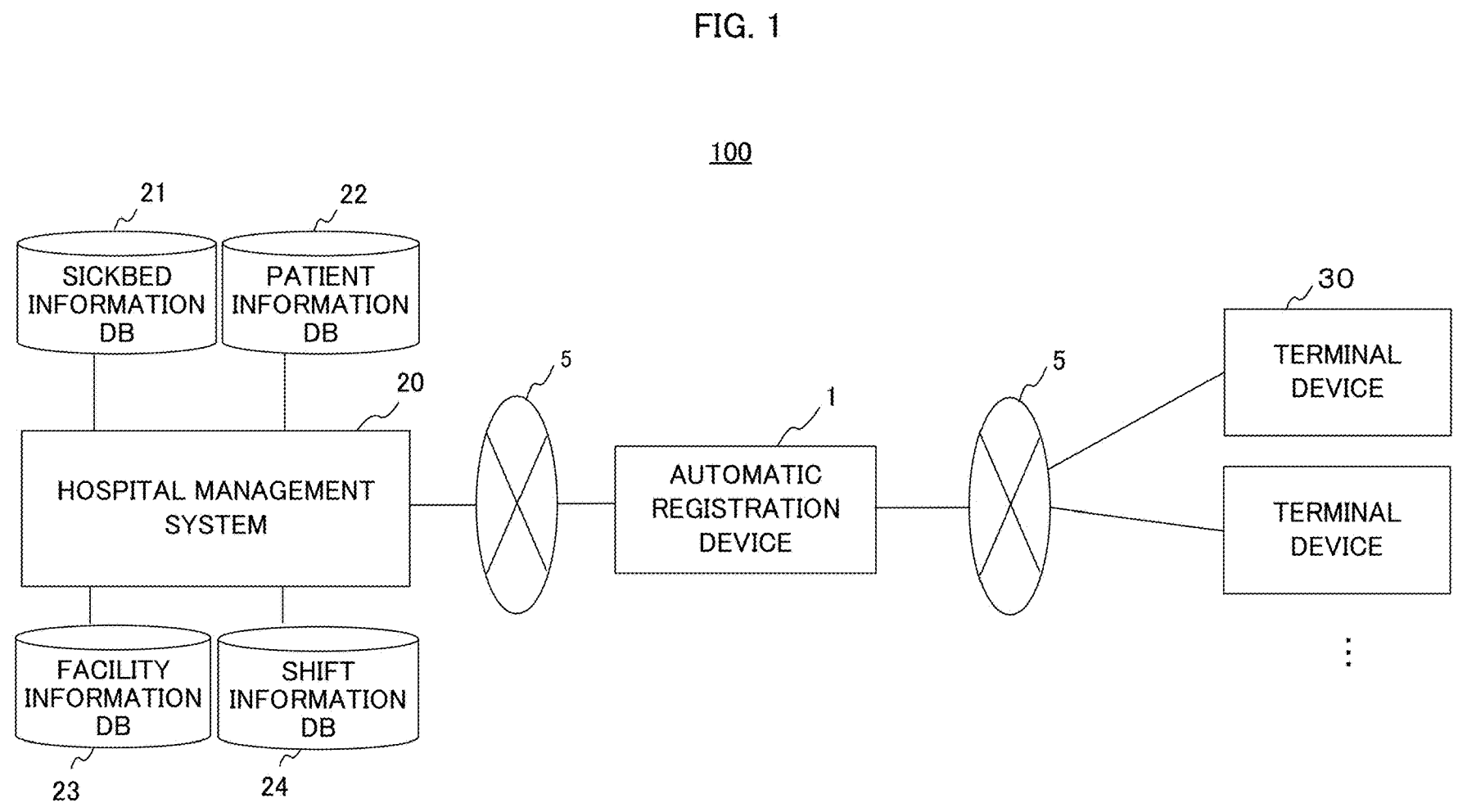

30 TERMINAL DEVICE

TERMINAL DEVICE

...

5

1 AUTOMATIC REGISTRATION DEVICE

5

20 HOSPITAL MANAGEMENT SYSTEM

22 PATIENT INFORMATION DB

21 SICKBED INFORMATION DB

24 SHIFT INFORMATION DB

23 FACILITY INFORMATION DB

FIG. 4

SICKBED INFORMATION

| SICKBED ID | DATE | AVAILABILITY STATE | PATIENT ROOM NUMBER | PATIENT ROOM TYPE |
|---|---|---|---|---|
| A001 | 8/10 | × | 101 | PRIVATE ROOM |
| | 8/11 | ○ | | |
| | ⋮ | ⋮ | | |
| A002 | 8/10 | × | 102 | FOUR-PERSON ROOM |
| | 8/11 | × | | |
| | ⋮ | ⋮ | | |
| A003 | 8/10 | ○ | | |
| | 8/11 | × | | |
| | ⋮ | ⋮ | | |
| ⋮ | ⋮ | ⋮ | | |
| ⋮ | ⋮ | ⋮ | ⋮ | ⋮ |

FIG. 5

PATIENT INFORMATION

| PATIENT ID | GENDER | AGE | DISEASE NAME | SEVERITY (1 to 3) | SICKBED ID | DATE OF DISCHARGE |
|---|---|---|---|---|---|---|
| B001 | MALE | 28 | INFLUENZA | 1 | — | 8/8 |
| B001 | FEMALE | 55 | ACUTE BRONCHITIS | 2 | A007 | UNDECIDED |
| B003 | MALE | 72 | ACUTE BRONCHITIS | 3 | A010 | UNDECIDED |
| ⋮ | ⋮ | ⋮ | ⋮ | ⋮ | ⋮ | ⋮ |

FIG. 6

FACILITY INFORMATION

| FACILITY ID | DATE | AVAILABILITY STATE | FACILITY NAME | DISEASE NAME | SEVERITY |
|---|---|---|---|---|---|
| C001 | 8/10 | × | VENTILATOR | PNEUMONIA, BRONCHITIS, RESPIRATORY FAILURE, … | 3 |
| | 8/11 | × | | | |
| | ⋮ | ⋮ | | | |
| C002 | 8/10 | ○ | OXYGEN MASK | PNEUMONIA, BRONCHITIS, RESPIRATORY FAILURE, … | 2 |
| | 8/11 | ○ | | | |
| | ⋮ | ⋮ | | | |
| ⋮ | ⋮ | ⋮ | ⋮ | ⋮ | ⋮ |

FIG. 7

SHIFT INFORMATION

| STAFF ID | JOB TITLE | RESPONDABLE SEVERITY (1 to 3) | WORKING DATA |
|---|---|---|---|
| D01 | PHYSICIAN (RESPIRATORY) | 3 | WORKING DATA D01 |
| D02 | PHYSICIAN (GASTROENTEROLOGY) | 3 | WORKING DATA D02 |
| ⋮ | ⋮ | ⋮ | ⋮ |
| E01 | NURSE | 3 | WORKING DATA E01 |
| E02 | NURSE | 2 | WORKING DATA E02 |
| ⋮ | ⋮ | ⋮ | ⋮ |

| Sun | Mon | Tue | Wed | Thu | Fri | Sat |
|---|---|---|---|---|---|---|
| 1 X | 2 X | 3 X | 4 X | 5 X | 6 X | 7 X |
| 8 X | 9 X | 10 3 pts | 11 1 pt | 12 2 pts | 13 X | 14 X |
| 15 X | 16 3 pts | 17 2 pts | 18 2 pts | 19 X | 20 2 pts | 21 3 pts |
| 22 3 pts | 23 1 pt | 24 X | 25 3 pts | 26 X | 27 1 pt | 28 3 pts |
| 29 X | 30 1 pt | 31 X | | | | |

INFORMATION PROCESSING DEVICE, INFORMATION PROCESSING METHOD, AND RECORDING MEDIUM

This application is a National Stage Entry of PCT/JP2022/003335 filed on Jan. 28, 2022, the contents of all of which are incorporated herein by reference, in their entirety.

TECHNICAL FIELD

The present disclosure relates to optimizing of resources of medical institutions.

BACKGROUND ART

In a case where a patient is admitted or transferred to a predetermined medical institution, various sets of information concerning facilities, which includes availability states of sickbeds, are needed to match a patient with each medical institution. Conventionally, a process for collecting and confirming information of the facility has been conducted via telephone, by a staff of a community relations office or an organization in a hospital having that function. Moreover, Patent Document 1 describes a sickbed use state management system for sharing information among users by centrally managing use states of sickbeds in institutions for inpatients.

PRECEDING TECHNICAL REFERENCES

Patent Document

Patent Document 1: U.S. Pat. No. 6,908,952

SUMMARY

Problem to be Solved by the Invention

With aging society, an important issue is how to effectively use limited resources of medical institutions. For example, it is possible to effectively use resources of local medical institutions by properly matching each patient with core hospitals, local hospitals, and clinics by the community relation.

In the matching of each patient with medical institutions, a conventional manner of collecting and confirming information by telephone is burdensome and inefficient on social workers and other staff. The sickbed use state management system described in Patent Document 1 can automatically collect information of the use sate of sickbeds; however, there is a case in which it may not be able to accept the patient due to various states even if the sickbed is available, and thus it is necessary to check again by staff using a telephone or the like.

It is one object of the present disclosure to effectively utilize the resources of medical institutions by automatically collecting information of the medical institutions and appropriately matching each patient and respective medical institutions.

Means for Solving the Problem

According to an example aspect of the present disclosure, there is provided an information processing device including:

- a sickbed information acquisition means configured to acquire sickbed information concerning use states of sickbeds in each of hospitals;
- a patient information acquisition means configured to acquire patient information concerning patients of the hospitals;
- a facility information acquisition means configured to acquire facility information concerning use states of facilities of each of the hospitals;
- a shift information acquisition means configured to acquire shift information concerning a work shift of medical professionals working at the hospitals;
- a sickbed availability prediction means configured to predict availability states of the sickbeds based on the sickbed information and the patient information;
- an unacceptable patient prediction means configured to predict unacceptable patients whom each of the hospitals cannot accept, based on the patient information, the facility information, and the shift information; and
- an acceptable patient information generation means configured to generate acceptable patient information concerning acceptable patients whom each of the hospitals can accept, based on the availability states of the sickbeds and the unacceptable patients which are predicted.

According to another example aspect of the present disclosure, there is provided an information processing method including:

- acquiring sickbed information concerning use states of sickbeds in each of hospitals;
- acquiring patient information concerning patients of the hospitals;
- acquiring facility information concerning use states of facilities of each of the hospitals;
- acquiring shift information concerning a work shift of medical professionals working at the hospitals;
- predicting availability states of the sickbeds based on the sickbed information and the patient information;
- predicting unacceptable patients whom each of the hospitals cannot accept, based on the patient information, the facility information, and the shift information; and
- generating acceptable patient information concerning acceptable patients whom the hospitals can accept, based on the availability states of the sickbeds and the unacceptable patients which are predicted.

According to still another example aspect of the present disclosure, there is provided a recording medium storing a program, the program causing a computer to perform a process including:

- acquiring sickbed information concerning use states of sickbeds in each of hospitals;
- acquiring patient information concerning patients of the hospitals;
- acquiring facility information concerning use states of facilities of each of the hospitals;
- acquiring shift information concerning a work shift of medical professionals working at the hospitals;
- predicting availability states of the sickbeds based on the sickbed information and the patient information;
- predicting unacceptable patients whom each of the hospitals cannot accept, based on the patient information, the facility information, and the shift information; and
- generating acceptable patient information concerning acceptable patients whom the hospitals can accept, based on the availability states of the sickbeds and the unacceptable patients which are predicted.

Effect of the Invention

According to the present disclosure, it becomes possible to effectively use resources of medical institutions by automatically collecting information of the medical institutions and appropriately matching each patient and respective medical institutions.

BRIEF DESCRIPTION OF THE DRAWINGS

FIG. 1 illustrates a configuration of an automatic registration system.

FIG. 4 illustrates an example of a data configuration of sickbed information.

FIG. 5 illustrates an example of a data configuration of patient information.

FIG. 6 illustrates an example of a data configuration of facility information.

FIG. 7 illustrates an example of a data configuration of shift information.

EXAMPLE EMBODIMENTS

Figure 2:
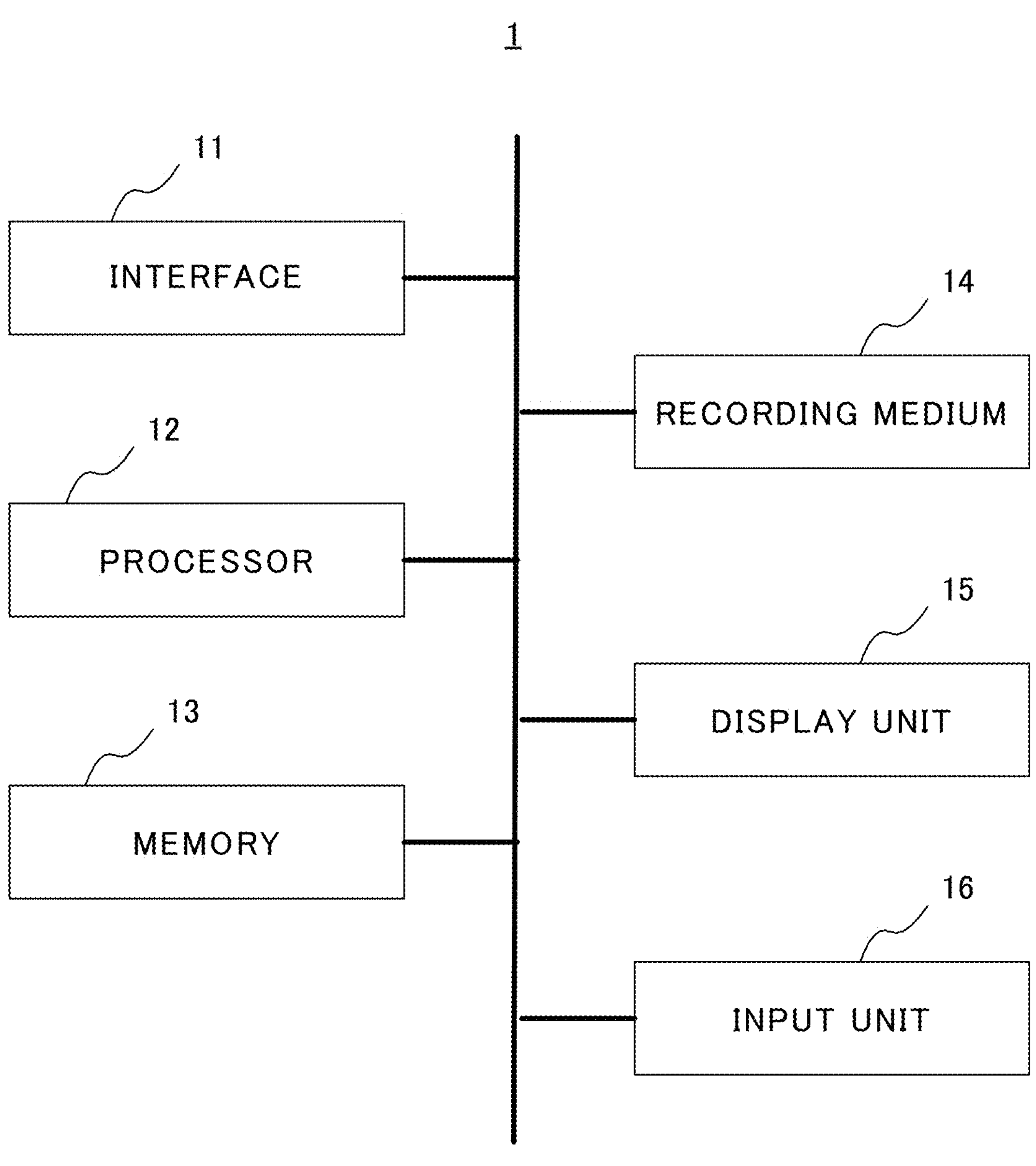
FIG. 2 illustrates a hardware configuration of an automatic registration device.

In the following, example embodiments will be described with reference to the accompanying drawings.

First Example Embodiment

Configuration

FIG. 1 illustrates a configuration of an automatic registration system to which an automatic registration device in the present disclosure is applied. An automatic registration system 100 is a system which acquires various information concerning hospitals, and generates and registers acceptable patient information concerning a patient (hereinafter referred to as an "acceptable patient") whom the hospital can accept. The automatic registration system 100 includes an automatic registration device 1, a hospital management system 20, and a terminal device 30, which are mutually communicably connected through a network 5 such as the Internet.

The automatic registration device 1 is an information processing device which processes, stores, transmits, and receives various types of information, and is, for instance, a server device, a personal computer, or a general-purpose tablet PC (personal computer). Specifically, the automatic registration device 1 acquires information concerning the hospitals from the hospital management system 20, generates and registers the acceptable patient information. Then, the automatic registration device 1 generates and outputs an acceptance state screen for matching each patient and the hospitals based on the registered acceptable patient information.

The hospital management system 20 is formed by one or more information processing devices, and is a system for processing, storing, transmitting and receiving various information concerning the hospitals. As described in detail below, the hospital management system 20 includes a hospital information database (hereinafter, also referred to as a "DB") 21, a patient information DB 22, a facility information DB 23, and a shift information DB 24.

The terminal device 30 is used by a user who matches the patient and the hospitals, for instance, and may be a wearable device such as a smart phone or a mobile phone, a tablet, an information processing device such as a PC terminal, or the like. Specifically, the terminal device 30 makes a screen request by communicating with the automatic registration device 1, and displays the acceptance state screen.

FIG. 2 is a block diagram illustrating a hardware configuration of the automatic registration device 1. As illustrated, the automatic registration device 1 includes an interface (Interface) 11, a processor 12, a memory 13, a recording medium 14, a display unit 15, and an input unit 16.

The interface 11 exchanges data with the hospital management system 20 and the terminal device 30 via the network 5. The interface 11 is used when receiving information concerning the hospitals from the hospital management system 20 and transmitting the acceptance state screen to the terminal device 30. Moreover, the interface 11 is used when the automatic registration device 1 transmits and receives data to and from a predetermined device which is connected by a wire or wireless communication.

The processor 12 is a computer such as a CPU (Central Processing Unit), and controls the entire automatic registration device 1 by executing programs prepared in advance. The memory 13 is formed by a ROM (Read Only Memory) and a RAM (Random Access Memory). The memory 13 stores the programs executed by the processor 12. Moreover, the memory 13 is used as a working memory during executions of various processes by the processor 12.

The recording medium 14 is a non-volatile and non-transitory recording medium such as a disk-shaped recording medium, a semiconductor memory, or the like, and is configured to be detachable to the automatic registration device 1. The recording medium 14 records various programs executed by the processor 12. When the automatic registration device 1 executes an automatic registration process or a correction and update process, the programs recorded in the recording medium 14 are loaded into the memory 13 and executed by the processor 12.

The display unit 15 is, for instance, an LCD (Liquid Crystal Display), and displays a predetermined screen. The input unit 16 is a keyboard, a mouse, a touch panel, or the like, and is used by an operator who manages the automatic registration device 1.

Figure 3:
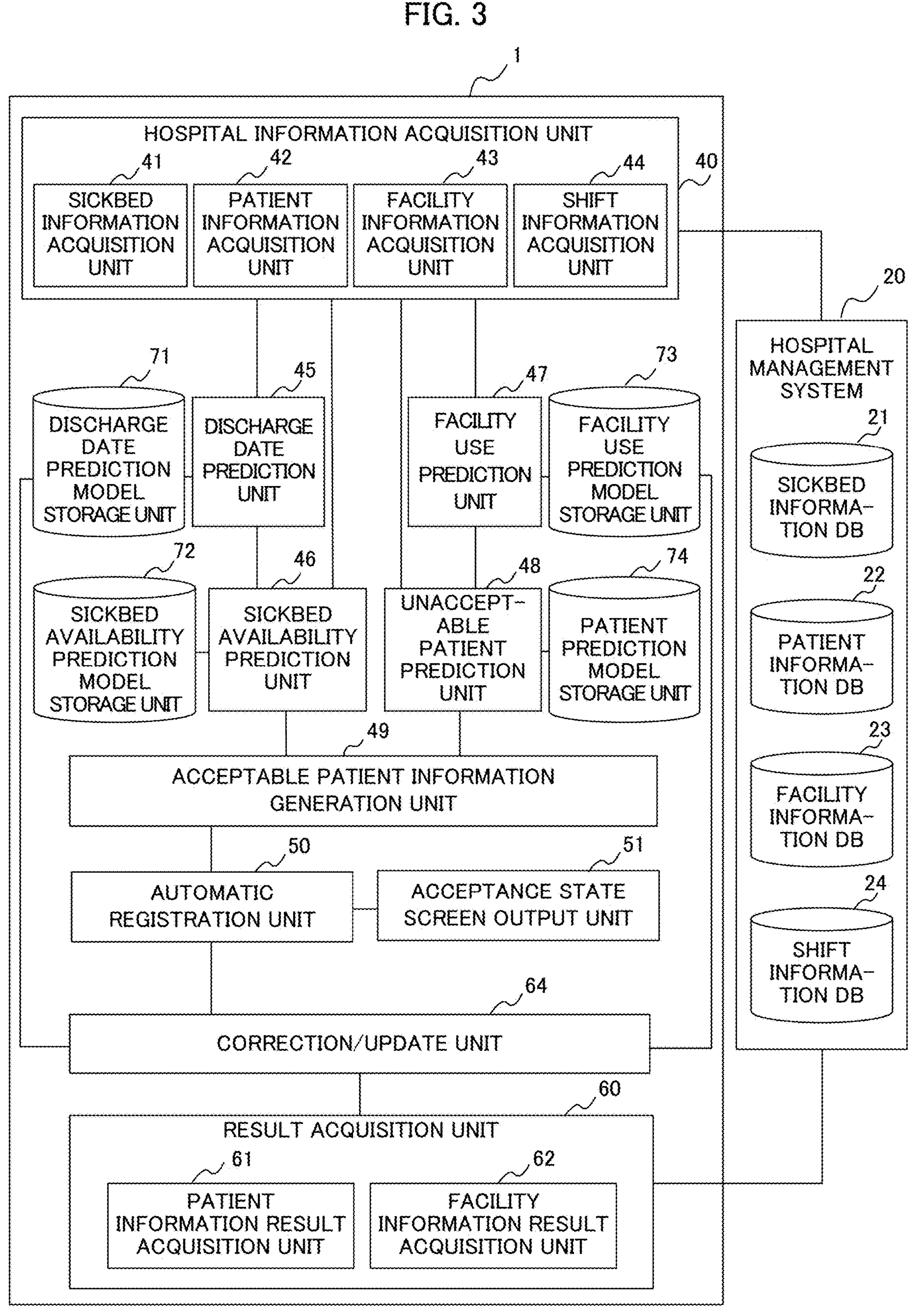
FIG. 3 illustrates a functional configuration of the automatic registration device.

FIG. 3 is a block diagram illustrating the functional configuration of the automatic registration device 1. The automatic registration device 1 functionally includes a hospital information acquisition unit 40, a discharge date prediction unit 45, a sickbed availability prediction unit 46, a facility use prediction unit 47, an unacceptable patient prediction unit 48, an acceptable patient information generation unit 49, an automatic registration unit 50, an acceptance state screen output unit 51, a result acquisition unit 60, a correction/update unit 64, a discharge date prediction model storage unit 71, a sickbed availability prediction model storage unit 72, a facility use prediction model storage unit 73, and a patient prediction model storage unit 74. The hospital information acquisition unit 40, the discharge date prediction unit 45, the sickbed availability prediction unit 46, the facility use prediction unit 47, the unacceptable patient prediction unit 48, the acceptable patient information generation unit 49, the automatic registration unit 50, the acceptance state screen output unit 51, the result acquisition unit 60 and the correction/update unit 64 are realized by the processor 12 executing respective programs. Also, the discharge date prediction model storage unit 71, the sickbed availability prediction model storage unit 72, the facility use prediction model storage unit 73, and the patient prediction model storage unit 74 are realized by the memory 13.

The automatic registration device 1 generates and registers acceptable patient information based on various sets of information concerning the hospitals, which are acquired from the hospital management system 20. By the automatic registration device 1 which generates and outputs the acceptance state screen based on the registered information, it is possible for the user to easily perform matching of the hospitals with each patient.

The hospital management system 20 includes the sickbed information DB 21, the patient information DB 22, the facility information DB 23, and the shift information DB 24. The sickbed information DB 21 stores information concerning sickbeds which each hospital has. The patient information DB 22 stores information concerning each patient attending the hospital or being admitted to the hospital. The facility information DB 23 stores information concerning facilities of the hospitals. Here, the facilities include not only equipment used in examinations, such as chest X-ray machine, an MRI (Magnetic Resonance Imaging) machine, a CT (Computed Tomography) machine, and the like, but also equipment and instruments used in treatments such as a dialysis machine, an indwelling catheter, an oxygen mask, a ventilator, an insulin injection, an anti-cancer drug, and the like. The shift information DB 24 stores information concerning working dates and times of medical professionals working at the hospitals. Here, the medical professionals are considered to be physicians, nurses, radiology technicians, clinical engineering technicians, and the like, and are professionals engaged in the examination and the treatment of patients.

The hospital information acquisition unit 40 includes a sickbed information acquisition unit 41, a patient information acquisition unit 42, a facility information acquisition unit 43, and a shift information acquisition unit 44, and acquires various sets of information concerning the hospitals.

The sickbed information acquisition unit 41 acquires the sickbed information concerning sickbeds in a current state from the sickbed information DB 21 of the hospital management system 20. FIG. 4 is an example of a data configuration of the sickbed information. As illustrated in FIG. 4, the sickbed information includes information of a sickbed ID, a date, an availability state, a patient room number, and a patient room type. The sickbed ID is identification information of the sickbed owned by the hospital. The date and the availability state are information indicating whether each sickbed is used or available on that date, and "×" denotes that the sickbed is used and "○" denotes that the sickbed is available in FIG. 4. The patient room number is a number of the patient room where one or more sickbeds are installed. The patient room type is a type of the patient room such as a private room and a four-person room. Incidentally, the sickbed information may include not only information concerning the availability state per day but also information concerning the availability state per hour on each date. Thus, the information including the sickbed information can be arbitrarily set.

The patient information acquisition unit 42 acquires patient information concerning respective patients of the hospitals from the patient information DB 22 of the hospital management system 20. FIG. 5 is an example of a data configuration of the patient information. As illustrated in FIG. 5, the patient information includes information of a patient ID, a gender, an age, a disease name, a severity, the sickbed ID, and a discharge date. The patient ID is identification information of the patient attending the hospital or being admitted to the hospital. The gender, the age, the disease name, and the severity are a gender, age, a disease name, and a severity of the patient. Here, the severity indicates a life prognosis or a functional prognosis of the patient, and is expressed in three levels: mild "1", moderate "2" and severe "3" in the present example embodiment. The sickbed ID is identification information of the sickbed which the patient is using during the hospitalization, and a hyphen is indicated for a patient who is not admitted. The discharge date indicates a day when a patient admitted to the hospital is discharged, "undecided" is indicated for a patient being admitted to the hospital, and the hyphen is indicated only for a patient attending the hospital. Incidentally, the patient information is not limited to the above example, but may include, for instance, information of a surgery date of the patient, an expected discharge date, a pre-existing medical condition, a risk of disturbance, and the like. As described above, the information included in the patient information can be arbitrarily set.

The facility information acquisition unit 43 acquires facility information concerning the facilities of each hospital for a certain period of time from the facility information DB 23 of the hospital management system 20. In the present example embodiment, the certain period of time can be set arbitrarily, for instance, after a few hours, after half a day, after one week, after 10 days, after one month or the like, can be arbitrarily set. FIG. 6 illustrates an example of a data configuration of the facility information. As illustrated in FIG. 6, the facility information includes the information of a facility ID, a date, an availability state, a facility name, a disease name, and a severity. The facility ID is identification information of the facilities owned by the hospital. The date and the availability state are information indicating whether each facility is used or available on that date, and in FIG. 6, "×" denotes that the facility is used all day due to reservations or the like and "○" denotes that the facility is available on that date. The facility name is the name of the equipment or the instrument which is the facility. The disease name is a name of disease for which the facility is used. The severity is the severity of the patient using the facility.

Specifically, for a facility such as a chest X-ray machine or a MRI scanner used in the examination, since the facility may be used for a plurality of patients for all day, the availability state becomes "×" for a case where the facility is reserved in all hours. The facility information may include not only information of the availability state per day but also information concerning the availability state per hour on each date. In addition, regarding oxygen masks and ventilators used in the treatments, the number is limited, the availability state indicates "×" in a case where all equipment is used because of limited numbers. The facility information may include information concerning the number of pieces of available equipment on each date. Moreover, the equipment information may not include information of one of or both the disease name and the severity. Accordingly, the information included in the facility information can be arbitrarily set.

The shift information acquisition unit 44 acquires the shift information concerning a work shift of the medical professionals working in the hospital within a certain period of time, from the shift information DB 24 of the hospital management system 20. FIG. 7 is an example of a data configuration of the shift information. As illustrated in FIG. 7, the shift information includes information of a staff ID, a job type, a severity possible to be handled, and working data. The staff ID is identification information of each of the medical professionals working in the hospitals. The job type is a title of each medical professional, for instance, a physician, a nurse, a radiological technician, a clinical engineer, or the like. The severity possible to be handled is a severity of the patient which the medical professional can handle. The working data correspond to information concerning the date and time when the medical professional works.

Specifically, in a case of a patient with a moderate symptom who is using the oxygen mask, a wide variety of checks are required, such as a check whether a tracheal tube has been disconnected from a breathing circuit, which is difficult for a new nurse to handle. Moreover, even if there is an experienced nurse who can handle patients with moderate or severe diseases, there is a limit to the number of nurses who can be assigned to the patients. As such, the shift information includes information of the severity possible to be handled which indicates the severity of the patient possible to be handled by each medical professional. Incidentally, the shift information is not limited thereto, and may include information of a specialty and a skill level of each medical professional. Accordingly, the information that the shift information has can be arbitrarily set.

The discharge date prediction model storage unit 71 stores a discharge date prediction model which has learned a relationship between patient information of the patient being hospitalized and the discharge date. A learning algorithm may use any machine learning technique such as, for instance, a neural network, a SVM (Support Vector Machine, a logistic regression (Logistic Regression). Based on the patient information of predetermined patients acquired by the patient information acquisition unit 42, the discharge date prediction unit 45 predicts the discharge dates respective to the patients using a discharge date prediction model. Specifically, the discharge date prediction unit 45 predicts the discharge dates respective to the patients who is currently hospitalized.

The sickbed availability prediction model storage unit 72 stores an availability state prediction model which has learned a relationship between the sickbed information and the discharge dates and the availability state of sickbeds. The learning algorithm may use any machine learning technique such as, for instance, the neural network, the SVM, the logistic regression, or the like. The sickbed availability prediction unit 46 predicts the availability state of the sickbeds within a certain period of time, based on the sickbed information acquired by the sickbed information acquisition unit 41 and the discharge dates respectively predicted by the discharge date prediction unit 45 for the patients being currently hospitalized.

The predicted availability state of the sickbeds may include information of the date and the number of available sickbeds such as "three available sickbeds on August 10", for instance. Moreover, information of per-day basis may be used such as "three available sickbeds on August 10", or information of a given time unit may be used such as "one available sickbed at 10:00 on August 10, and three available sickbeds at 12:00 on August 10". A unit for predicting the availability state of the sickbeds is not limited to these, but may be arbitrarily set in a unit of a few days, a few weeks, or the like.

The facility use prediction model storage unit 73 stores a facility use prediction model which has learned a relationship between the patient information and the facility information and use states of facilities. The learning algorithm may use any machine learning technique such as the neural network, the SVM, the logistic regression, or the like, for instance. The facility use prediction unit 47 predicts the use states of the facilities within a certain period of time based on the patient information acquired by the patient information acquisition unit 42 and the facility information acquired by the facility information acquisition unit 43, using the facility use prediction model. Specifically, based on the patient information, the facility use prediction unit 47 predicts the use states of the facilities within the certain period of time in consideration of the facility which may be used for a patient and date and time to use that facility, depending on the severity, an operation date, and the like of the patient attending the hospital or being admitted to the hospital.

The facility use prediction unit 47 may use the facility use prediction model which has learned a relationship between the patient information and the facility information and the shift information and the use states of the facilities. According to this, it is possible for the facility use prediction unit 47 to predict the use states of the facilities based on the shift information acquired by the shift information acquisition unit 44 in consideration of the work shift of the medical professionals necessary to use the facility.

Each of the predicted use states of the facilities includes information of the date, the facility, and the availability such as "MRI scanner is available on August 10", for instance. Moreover, information of per-day basis may be used such as "MRI scanner is available on August 10", information of a given time unit may be used such as "MRI scanner is not available at 10:00 on August 10 and MRI scanner is available at 12:00 on August 10". A unit for predicting the availability state of each facility is not limited to these, but may be arbitrarily set in a unit of a few days, a few weeks, or the like.

The patient prediction model storage unit 74 stores the patient prediction model which has learned a relationship between the use states of the facilities and the shift information and a patient who cannot be accepted (also referred to as an "unacceptable patient"). The learning algorithm may use any machine learning technique, such as, for instance, the neural network, the SVM, the logistic regression, and the like. The unacceptable patient prediction unit 48 predicts the unacceptable patient based on the use states of the facilities predicted by the facility use prediction unit 47 and the shift information acquired by the shift information acquisition unit 44, using the patient prediction model. Specifically, the unacceptable patient prediction unit 48 predicts, based on the use of each facility, the patient who cannot be accepted because the facility necessary for the examination or the treatment is not available. Moreover, the unacceptable patient prediction unit 48 also predicts an the patient who cannot be accepted because there is no medical professional corresponding to the examination or the treatment.

Information concerning the unacceptable patient which is predicted includes a date and information of the patient who cannot be accepted such as a "patient using the ventilator because there is no available facility on August 10", or a "critically ill patient with disease ○○ in a lack of medical professionals on August 10", for instance. The information of the patient who cannot be accepted corresponds to information of the facility used for the patient, and information of the disease name and the severity of the patient.

In addition, the information concerning unacceptable patient which is predicted may be information on a daily basis such as the "patient using the ventilator because there is no available facility on August 10" or information on a predetermined time basis such as the "patient using the ventilator because there is no space in the equipment between 10:00 and 12:00 on August 10". The unit for predicting the unacceptable patient is not limited thereto, but can be set arbitrarily in a unit of a few days, a few weeks, or the like.

Based on the availability state of the sickbeds predicted by the sickbed availability prediction unit 46 and the unacceptable patient predicted by the unacceptable patient prediction unit 48, the acceptable patient information generation unit 49 determines whether the hospital can accept a newly admitted or transferred patient, and generates information concerning the patient who can be acceptable within a certain period of time as the acceptable patient information. The acceptable patient information includes information of the date or date and time on which the patient can be accepted, the number of patients who can be accepted, and patients who cannot be accepted.

Specifically, the acceptable patient information generation unit 49 determines that no patient can be accepted when there is no available sickbed. On the other hand, when there are the available sickbeds, the acceptable patient information generation unit 49 determines that patients who do not correspond to the unacceptable patients can be accepted. The acceptable patient information generation unit 49 can generate the acceptable patient information in any unit such as a unit of a few hours or a unit of one day.

The automatic registration unit 50 registers the acceptable patient information generated by the acceptable patient information generation unit 49. Specifically, the automatic registration unit 50 stores the acceptable patient information in the memory 13 or the like.

Based on the acceptable patient information registered by the automatic registration unit 50, the acceptance state screen output unit 51 generates and outputs the acceptance state screen which displays the date or the date and time when the hospital can accept the patients, the number of patients who can be accepted, and the information of the patients who cannot be accepted. Specifically, when the screen request is received from the terminal device 30, the acceptance state screen output unit 51 generates the acceptance state screen based on the acceptable patient information registered at that point, and transmits the generated acceptance state screen to the terminal device 30.

Figures 8A, 8B:
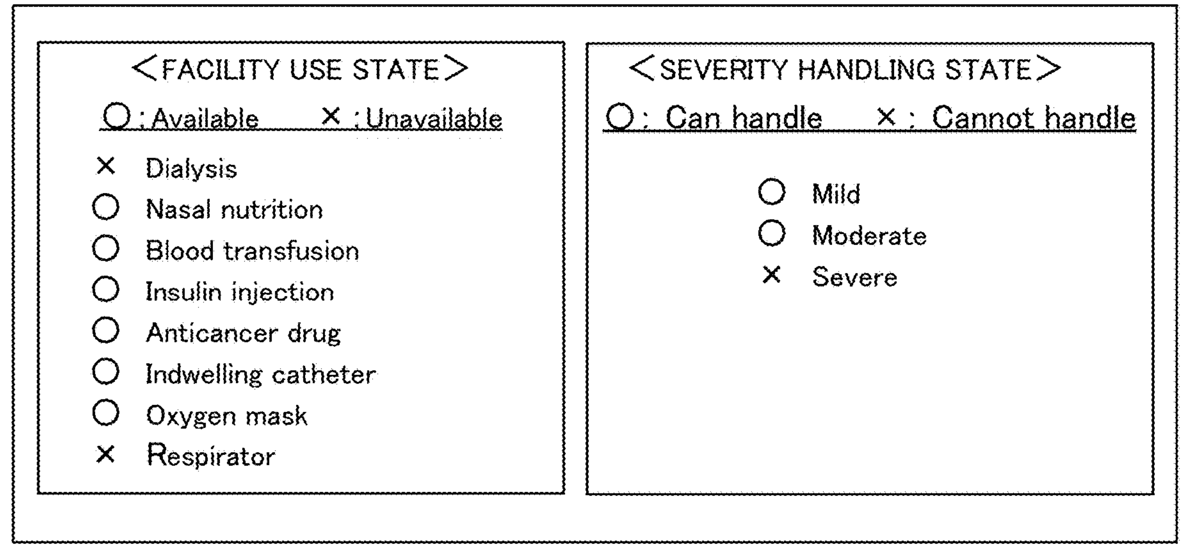
FIG. 8 illustrates an example of an acceptance state screen.

FIG. 8A and FIG. 8B are examples of the acceptance state screen. As illustrated in FIG. 8A, the acceptance state screen is designed similar to a calendar, and a box of each date is marked with a × mark or the number of patients. The × mark indicates that the patient cannot be accepted on that date. On the other hand, the number of patients represents a count of patients who can be accepted on that date. When the number of patients is clicked, information of patients who cannot be accepted on that date is displayed as illustrated in FIG. 8B. Specifically, information of unavailable facilities or the severity which cannot be handled is displayed as unacceptable patient information.

The acceptance state screen illustrated in FIG. 8 display the acceptance state for one month with a form similar to the calendar, but the present example embodiment is not limited thereto, the acceptance state screen may display the acceptance state of any period such as a few days or a few weeks and a form of the period can be arbitrarily set. Moreover, the acceptance state screen illustrated in FIG. 8 displays the acceptance state on a daily basis, but the present example embodiment is not limited thereto, and the acceptance state screen may display the acceptance state in any unit such as a few hours. Specifically, the period or unit of the acceptance state can be set by aa user using the terminal device 30, and information concerning settings may be included in the screen request. In this way, by changing the period and the unit for displaying the acceptance status, it is possible to display the acceptance state screen appropriate for the user in any case, for instance, a case of considering a long-term hospitalization, or a case of considering a recent half-day hospitalization for emergency surgery.

The result acquisition unit 60 includes a patient information result acquisition unit 61 and the facility information result acquisition unit 62, and acquires results concerning the discharge dates respective to the patients and the use states of the facilities. The patient information result acquisition unit 61 acquires the discharge date of each of the patients who have already been discharged from the patient information DB 22 of the hospital management system 20. In addition, the facility information acquisition unit 62 acquires not information of reservations but information of a state in which the facility is actually used, from the facility information DB 23 of the hospital management system 20.

Based on the discharge dates respective to the patients and the use states of the facilities acquired by the result acquisition unit 60, in a case where the discharge dates predicted by the discharge date prediction unit 45 or the use states of the facilities predicted by the facility use prediction unit 47 are incorrect, the correction/update unit 64 corrects the acceptable patient information which has been registered based on the results as appropriate. Moreover, in a case where the acceptable patient information is corrected, the correction/update unit 64 generates additional learning data in which the results acquired by the result acquisition unit 60 are considered as correct answers, and accumulates the additional learning data. Specifically, the correction/update unit 64 generates additional learning data, in which respective discharge dates when the patients are actually discharged are considered as the correct answers, and updates the discharge date prediction model using re-learning. In addition, the correction/update unit 64 generates additional learning data in which actual use states of the facilities are considered as the correct answers, and updates the facility use prediction model by performing re-learning. As described above, by these feedbacks of the actual results, it is possible to improve a prediction accuracy of the discharge date prediction model and the facility use prediction models.

Incidentally, for convenience of explanation, the hospital management system 20 includes a sickbed information DB 21, a patient information DB 22, a facility information DB 23, and a shift information DB 24; however, the present disclosure is not limited thereto, and since the hospital information acquisition unit 40 or the result acquisition unit 60 may acquire necessary information, each type of the DBs and each data configuration of the DBs are arbitrarily determined.

Automatic Registration Process

Figure 9:
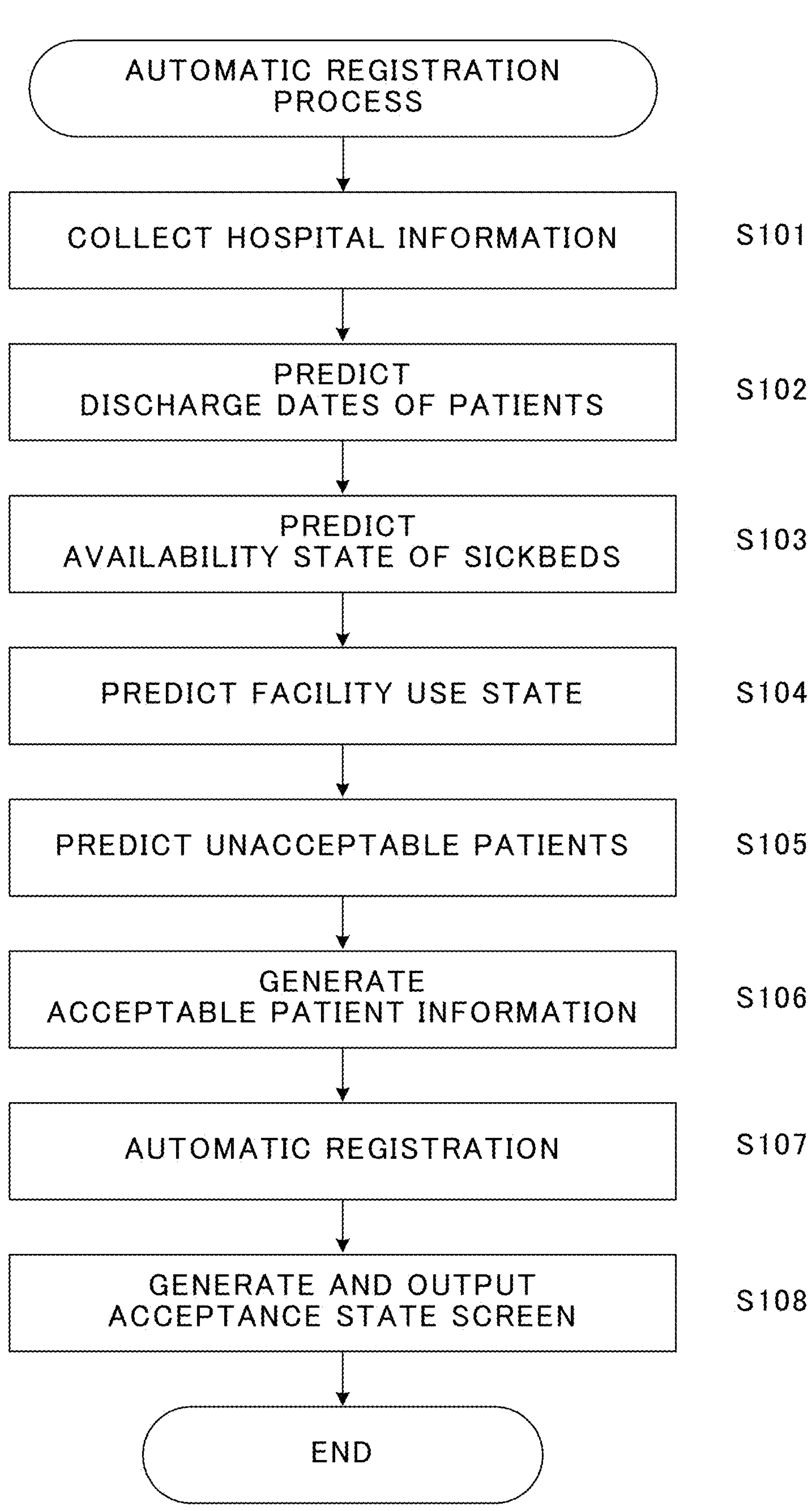
FIG. 9 illustrates a flowchart of an automatic registration process.

Next, the automatic registration process performed by the automatic registration device 1 will be described. FIG. 9 is a flowchart of the automatic registration process performed by the automatic registration device 1. This process is realized by the processor 12 illustrated in FIG. 2 which executes a program prepared in advance.

First, the automatic registration device 1 collects hospital information from the hospital management system 20 (step S101). Specifically, from the hospital management system 20, the automatic registration device 1 acquires the sickbed information concerning current sickbeds, the patient information concerning the patients of the hospital, the facility information concerning the facilities of each hospital within a certain period of time, and the shift information concerning the work shift within the certain period of time for the medical professionals working in the hospital.

The automatic registration device 1 predicts the discharge date of each patient currently hospitalized from the acquired patient information using the discharge date prediction model (step S102). Next, the automatic registration device 1 predicts the availability state of the sickbeds within a certain period of time from the acquired sickbed information and the predicted discharge date, using the availability state prediction model (step S103).

Moreover, the automatic registration device 1 predicts the use states of the facilities within the certain period of time based on the acquired patient information and the facility information, using the facility use prediction model (step S104). After that, the automatic registration device 1 predicts the unacceptable patients based on the use states of the facilities which are predicted and the acquired shift information, using the patient prediction model (step S105).

Next, the automatic registration device 1 determines whether or not the hospital can accept a newly admitted or transferred patient, based on the predicted availability state of the sickbeds and the unacceptable patient predicted by the unacceptable patient prediction unit 48, and generates information concerning each patient who can be accepted within a certain period of time as the acceptable patient information (step S106). The automatic registration device 1 registers the generated acceptable patient information (step S107). Subsequently, the automatic registration device 1 generates the acceptance state screen which displays the date or the date and time when the hospital can accept the patient, the number of patients who can be accepted, and the information concerning patients who cannot be accepted, based on the registered acceptability patient information, and outputs the generated acceptance state screen (step S108). Specifically, when a screen request is received from the terminal device 30, the automatic registration device 1 generates an acceptance state screen based on acceptable patient information registered at that time, and transmits the generated acceptance state screen to the terminal device 30. The user confirms information concerning the hospitals by the acceptance state screen displayed on the terminal device 30, performs matching between each patient and respective hospitals. Accordingly, the automatic registration process is terminated.

Correction/Update Process

Figure 10:
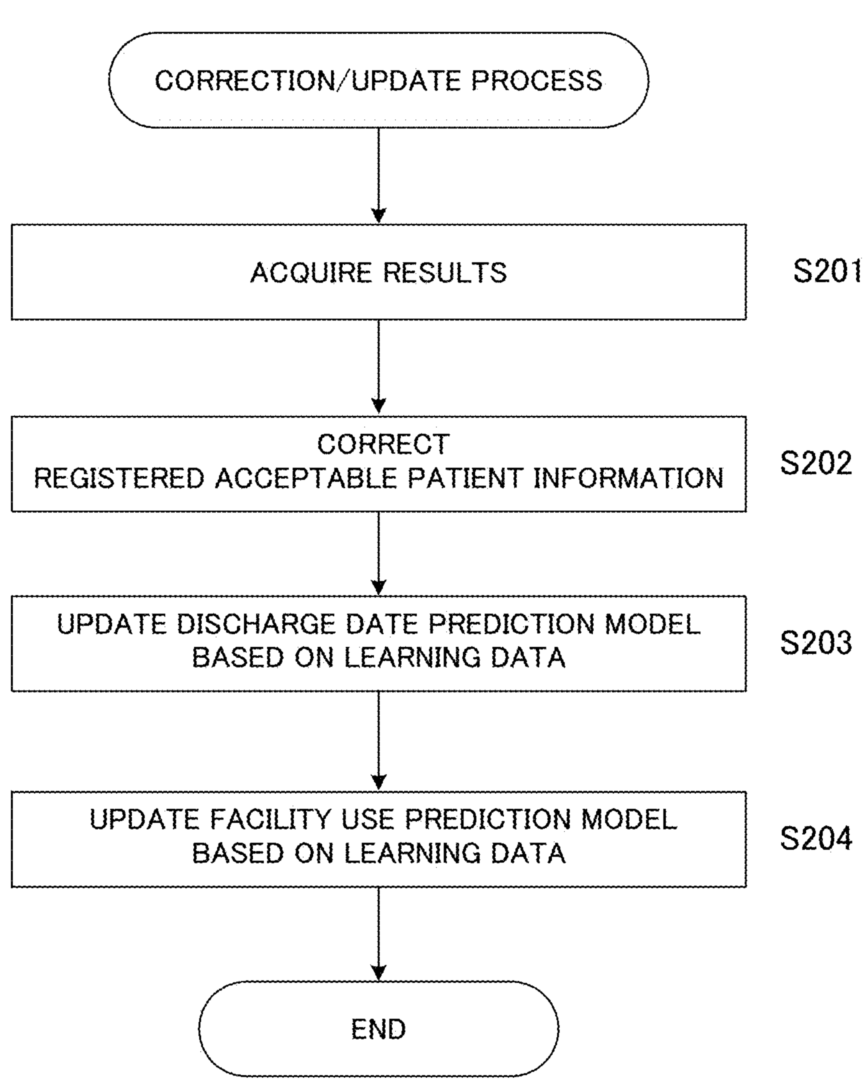
FIG. 10 illustrates a flowchart of a correction/update process.

Next, the correction/update process performed by the automatic registration device 1 will be described. FIG. 10 is a flowchart of the correction/update process performed by the automatic registration device 1. This process is realized by the processor 12 illustrated in FIG. 2 which executes a program prepared in advance.

First, the automatic registration device 1 acquires the discharge date and the use states of the facilities as results (step S201). Next, the automatic registration device 1 corrects the acceptable patient information which is registered, based on the results as appropriate, when the predicted discharge date of the patient and the predicted use states of the facilities do not correspond to the results (step S202). Furthermore, the automatic registration device 1 generates, based on the results, additional learning data in which the actual discharge date is considered as the correct answer, and updates the discharge date prediction model (step S203). In addition, based on the result, the automatic registration device 1 generates additional learning data in which the actual use states of the facilities are the correct answers, and updates the facility use prediction model (step S204). Accordingly, the modification update process is terminated.

Note that, in the present example embodiment, the correction/update process is performed by the automatic registration device 1; however, the present disclosure is not limited thereto, and the correction of the acceptable patient information and the updates of the discharge date prediction model and the facility use prediction model may be performed manually.

As described above, the automatic registration device 1 can automatically collect information of medical institutions such as the hospitals, and register information concerning the patient who can be accepted within the certain period of time. Then, it is possible to appropriately correct the registered information. Furthermore, based on the registered information, the automatic registration device 1 can output information concerning the patient whom each of the medical institutions can accept, as the acceptance state screen.

Since the certain period of time to display data on the acceptance state screen can be adjusted, it is possible to present the appropriate acceptance state not only for a case of the most recent emergency hospitalization but also for a case where the user is considering coordinating a hospital transfer after a week or half a month. Moreover, since the acceptance state screen displays information concerning each unavailable facility and the severity which cannot be handled as information concerning the patients who cannot be accepted, it is possible for the user to match each of the patients who meet conditions of the facilities and the severity, with the medical institutions. Therefore, it is possible for the user to efficiently match each of the patients with the medical institutions and to effectively use resources of the medical institutions.

Second Example Embodiment

Figure 11:
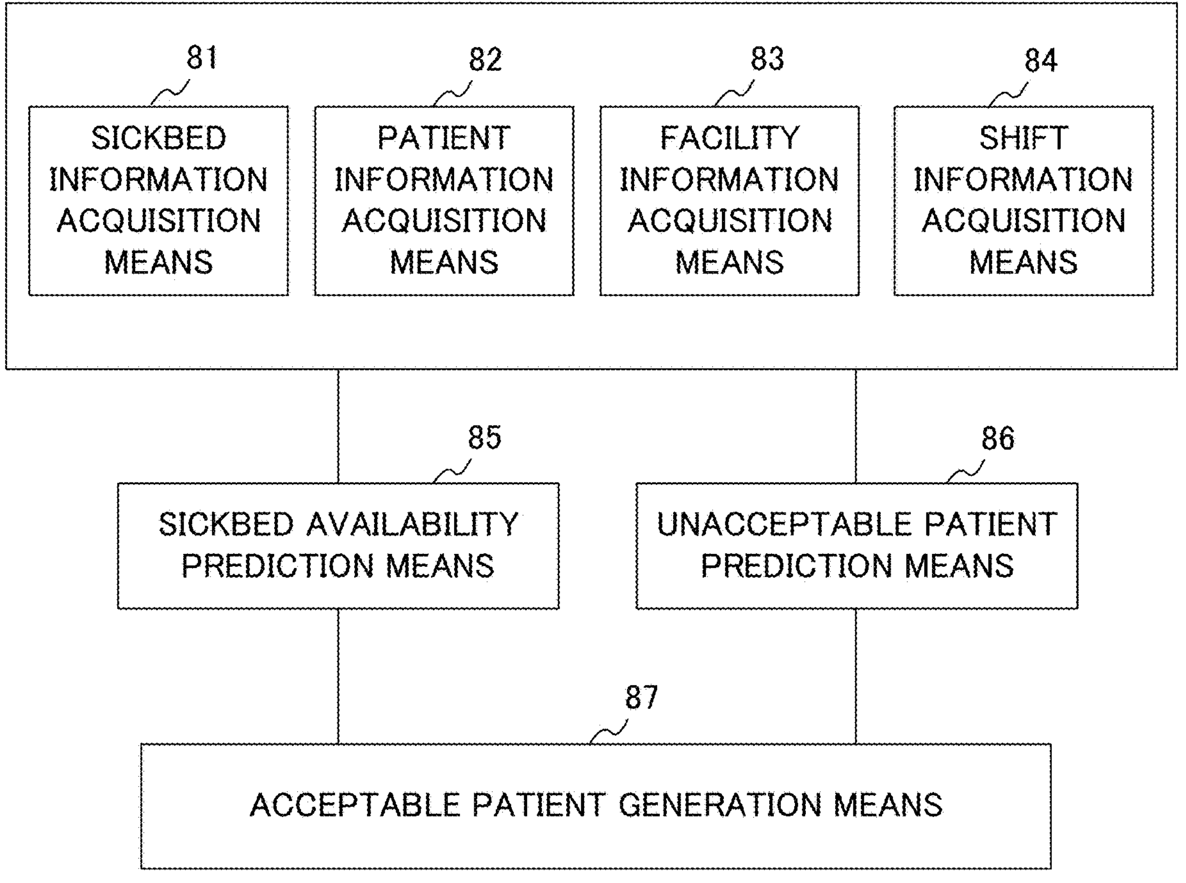
FIG. 11 illustrates a functional configuration of an information processing device according to a second example embodiment.

FIG. 11 is a block diagram illustrating a functional configuration of an information processing device according to a second example embodiment. An information processing device 80 includes a sickbed information acquisition means 81, a patient information acquisition means 82, a facility information acquisition means 83, a shift information acquisition means 84, a sickbed availability prediction means 85, an unacceptable patient prediction means 86, and an acceptable patient information generation means 87.

Figure 12:
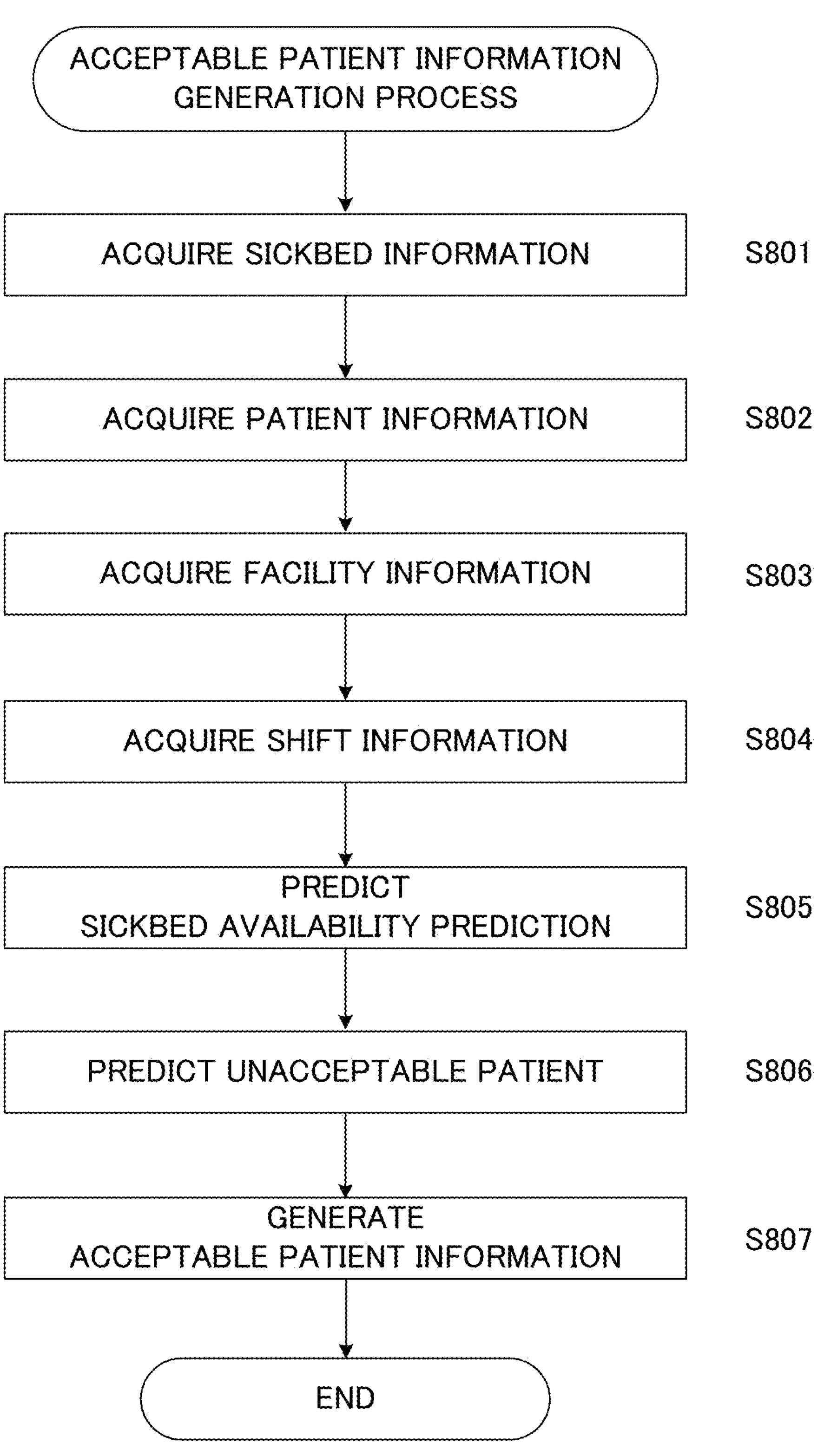
FIG. 12 illustrates a flowchart of a process performed by an information processing device according to the second example embodiment.

FIG. 12 is a flowchart of an acceptable patient information generation process performed by the information processing device 80. The sickbed information acquisition means 81 acquires the sickbed information concerning use states of the sickbeds in each hospital (step S801). The patient information acquisition means 82 acquires the patient information concerning patients of the hospitals (step S802). The facility information acquisition means 83 acquires the facility information concerning the use states of the facilities in hospitals (step S803). The shift information acquisition means 84 acquires the shift information concerning the work shift of the medical professionals working at the hospitals (step S804). The sickbed availability prediction means 85 predicts the availability state of the sickbeds based on the sickbed information and the patient information (step S805). The unacceptable patient prediction means 86 predicts the unacceptable patient whom each hospital cannot accept, based on the patient information, the facility information, and the shift information (step S806). The acceptable patient information generation means 87 generates the acceptable patient information concerning the acceptable patient whom each hospital can accept, based on information of the predicted availability state of the sickbeds and the predicted unacceptable patient (step S807).

According to the information processing device 80 of the second example embodiment, it is possible to efficiently perform the matching of each patient and respective medical institutions based on the acceptable patient information.

A part or all of the example embodiments described above may also be described as the following supplementary notes, but not limited thereto.

Supplementary Note 1

An information processing device comprising:

a sickbed information acquisition means configured to acquire sickbed information concerning use states of sickbeds in each of hospitals;

a patient information acquisition means configured to acquire patient information concerning patients of the hospitals;

a facility information acquisition means configured to acquire facility information concerning use states of facilities of each of the hospitals;

a shift information acquisition means configured to acquire shift information concerning a work shift of medical professionals working at the hospitals;

a sickbed availability prediction means configured to predict availability states of the sickbeds based on the sickbed information and the patient information;

an unacceptable patient prediction means configured to predict unacceptable patients whom each of the hospitals cannot accept, based on the patient information, the facility information, and the shift information; and an acceptable patient information generation means configured to generate acceptable patient information concerning acceptable patients whom each of the hospitals can accept, based on the availability states of the sickbeds and the unacceptable patients which are predicted.

Supplementary Note 2

The information processing device according to supplementary note 1, further comprising a discharge date prediction means configured to predict discharge dates respective to the patients based on the patient information, wherein the sickbed availability prediction means predicts the availability states of the sickbeds based on the sickbed information and the discharge dates which are predicted.

Supplementary Note 3

The information processing device according to supplementary note 1 or 2, further comprising a facility use prediction means configured to predict the use states of the facilities based on the patient information and the facility information, wherein the unacceptable patient prediction means predicts the unacceptable patients based on the shift information and the use states of the facilities which are predicted.

Supplementary Note 4

The information processing device according to any one of supplementary notes 1 to 3, wherein the patient information includes information concerning at least one of a disease name and a severity of each of the patients;

the facility information includes information concerning at least of the disease name and the severity to use each facility;

the shift information includes information of the severity which the medical professionals can handle; and the unacceptable patient prediction means predicts the unacceptable patients based on at least one of the disease name and the severity.

Supplementary Note 5

The information processing device according to any one of supplementary notes 1 to 4, further comprising an acceptance state screen output means configured to generate and output an acceptance state screen which displays a date or a date and time when each hospital can accept the patients, the number of the patients who can be accepted, and information of the patients who cannot be accepted, based on the acceptable patient information.

Supplementary Note 6

The information processing device according to supplementary note 5, wherein the acceptance state screen displays information concerning each facility to be used for the unacceptable patients.

Supplementary Note 7

The information processing device according to any one of supplementary notes 3 to 6, wherein the information processing device is communicatively connected to a hospital management system which manages information concerning the hospitals, and the sickbed information acquisition means, the patient information acquisition means, the facility information acquisition means, and the shift information acquisition means respectively acquire the sickbed information, the patient information, the facility information, and the shift information, from the hospital management system, wherein the information processing device further comprises a result acquisition means configured to acquire the discharge dates respective to the patients and the use states of the facilities as results, from the hospital management system; and a correction means configured to correct the acceptable patient information based on the results.

Supplementary Note 8

The information processing device according to supplementary note 7, wherein the discharge date prediction means predicts the discharge dates respective to the patients using a discharge date prediction model which is trained by machine learning in advance, and the unacceptable patient prediction means predicts a patient whom each of the hospitals cannot accept, using a patient prediction model which is trained by the machine learning in advance, wherein the information processing device further comprises an update means configured to generate additional learning data in which the discharge dates respective to the patients based on the results are considered as correct answers, and additional learning data in which the use states of the facilities based on the results are considered as correct answers, and to update the discharge date prediction model and the patient prediction model respectively.

Supplementary Note 9

An information processing method comprising:

acquiring sickbed information concerning use states of sickbeds in each of hospitals;

acquiring patient information concerning patients of the hospitals;

acquiring facility information concerning use states of facilities of each of the hospitals;

acquiring shift information concerning a work shift of medical professionals working at the hospitals;

predicting availability states of the sickbeds based on the sickbed information and the patient information;

predicting unacceptable patients whom each of the hospitals cannot accept, based on the patient information, the facility information, and the shift information; and generating acceptable patient information concerning acceptable patients whom the hospitals can accept, based on the availability states of the sickbeds and the unacceptable patients which are predicted.

Supplementary Note 10

A recording medium storing a program, the program causing a computer to perform a process comprising:

acquiring sickbed information concerning use states of sickbeds in each of hospitals;

acquiring patient information concerning patients of the hospitals;

acquiring facility information concerning use states of facilities of each of the hospitals;

acquiring shift information concerning a work shift of medical professionals working at the hospitals;

predicting availability states of the sickbeds based on the sickbed information and the patient information;

predicting unacceptable patients whom each of the hospitals cannot accept, based on the patient information, the facility information, and the shift information; and generating acceptable patient information concerning acceptable patients whom the hospitals can accept, based on the availability states of the sickbeds and the unacceptable patients which are predicted.

While the disclosure has been described with reference to the example embodiments and examples, the disclosure is not limited to the above example embodiments and examples. It will be understood by those of ordinary skill in the art that various changes in form and details may be made therein without departing from the spirit and scope of the present disclosure as defined by the claims.

DESCRIPTION OF SYMBOLS

1 Automatic registration device
5 Network
11 Interface
12 Processer
13 Memory
14 Recording medium
15 Display unit
16 Input unit
20 Hospital management system
21 Sickbed information DB
22 Patient information DB
23 Facility information DB
24 Shift information DB
30 Terminal device
40 Hospital information acquisition unit
45 Discharge date prediction unit
46 Sickbed availability prediction unit
47 Facility use prediction unit
48 Unacceptable patient prediction unit
49 Acceptable patient information generation unit
50 Automatic registration unit
51 Acceptance state screen output unit
60 Result acquisition unit
64 Correction/update unit

What is claimed is:

1. An information processing device which is communicatively connected to a hospital management system which manages information concerning hospitals, the information processing device comprising:

at least one memory configured to store instructions; and at least one processor configured to execute the instructions to:

acquire sickbed information concerning use states of sickbeds in each of the hospitals, from the hospital management system;

acquire patient information concerning patients of the hospitals, from the hospital management system;

acquire facility information concerning use states of facilities of each of the hospital, from the hospital management system;

acquire shift information concerning a work shift of medical professionals working at the hospitals, from the hospital management system;

predict discharge dates respective to the patients based on the acquired patient information;

predict availability states of the sickbeds within a certain period of time, based on the predicted discharge dates and the facility information;

predict the use states of the facilities within the certain period of time based on the acquired patient information and the acquired facility information, predict unacceptable patients whom each of the hospitals cannot accept, based on the use states of the facilities and the shift information within the certain period of time;

generate acceptable patient information concerning acceptable newly admitted or transferred patients whom each of the hospitals can accept, based on the availability states of the sickbeds and the unacceptable patients which are predicted;

acquire discharge dates respective to the patients and the use states of the facilities as results, from the hospital management system; and correct the acceptable patient information based on the results in a case where the predicted discharge dates and the predicted use states of the facilities are different from the results.

2. The information processing device according to claim 1, wherein the at least one processor further configured to:

predict the availability states of the sickbeds based on the sickbed information and the discharge dates which are predicted.

3. The information processing device according to claim 1, wherein the patient information includes information concerning at least one of a disease name and a severity of each of the patients;

the facility information includes information concerning at least of the disease name and the severity to use each facility;

the shift information includes information of the severity which the medical professionals can handle; and the at least one processor predicts the unacceptable patients each for whom a facility necessary for each examination or a corresponding treatment is not available, based on the use states of the facilities.

4. The information processing device according to claim 1, wherein the at least one processor is further configured to generate and output an acceptance state screen which displays a date or a date and time when each hospital can accept the patients, the number of the patients who can be accepted, and information of the patients who cannot be accepted and matches each patient and respective hospitals, based on the acceptable patient information.

5. The information processing device according to claim 4, wherein the acceptance state screen displays information of unavailable facilities or a severity which cannot be handled, as information concerning the unacceptable patients.

6. The information processing device according to claim 1, wherein the at least one processor is further configured to:

predict the discharge dates respective to the patients using a discharge date prediction model which is trained by machine learning in advance, predict the use states of the facilities within the certain period of time based on the acquired patient information and the acquired facility information by using a facility use prediction model, and generate additional learning data in which the discharge dates respective to the patients based on the results are considered as correct answers, and additional learning data in which the use states of the facilities based on the results are considered as correct answers, and to update the discharge date prediction model and the facility use prediction model respectively.

7. An information processing method comprising:

acquiring sickbed information concerning use states of sickbeds in each of hospitals, from a hospital management system which manages information concerning the hospitals;

acquiring patient information concerning patients of the hospitals, from the hospital management system;

acquiring facility information concerning use states of facilities of each of the hospitals, from the hospital management system;

acquiring shift information concerning a work shift of medical professionals working at the hospitals, from the hospital management system;

predicting discharge dates respective to the patients based on the acquired patient information;

predicting availability states of the sickbeds within a certain period of time, based on the predicted discharge dates and the facility information;

predicting the use states of the facilities within the certain period of time based on the acquired patient information and the acquired facility information, predicting unacceptable patients whom each of the hospitals cannot accept, based on the use states of the facilities and the shift information within the certain period of time;

generating acceptable patient information concerning acceptable newly admitted or transferred patients whom the hospitals can accept, based on the availability states of the sickbeds and the unacceptable patients which are predicted;

acquiring discharge dates respective to the patients and the use states of the facilities as results, from the hospital management system; and correcting the acceptable patient information based on the results in a case where the predicted discharge dates and the predicted use states of the facilities are different from the results.

8. A non-transitory computer-readable recording medium storing a program, the program causing a computer to perform a process comprising:

acquiring sickbed information concerning use states of sickbeds in each of hospitals, from a hospital management system which manages information concerning the hospitals;

acquiring patient information concerning patients of the hospitals, from the hospital management system;

acquiring facility information concerning use states of facilities of each of the hospitals, from the hospital management system;

acquiring shift information concerning a work shift of medical professionals working at the hospitals, from the hospital management system;

predicting discharge dates respective to the patients based on the acquired patient information;

predicting availability states of the sickbeds within a certain period of time, based on the predicted discharge dates and the facility information;

predicting the use states of the facilities within the certain period of time based on the acquired patient information and the acquired facility information, predicting unacceptable patients whom each of the hospitals cannot accept, based on the use states of the facilities and the shift information within the certain period of time;

generating acceptable patient information concerning acceptable newly admitted or transferred patients whom the hospitals can accept, based on the availability states of the sickbeds and the unacceptable patients which are predicted;

acquiring discharge dates respective to the patients and the use states of the facilities as results, from the hospital management system; and correcting the acceptable patient information based on the results in a case where the predicted discharge dates and the predicted use states of the facilities are different from the results.

* * * * *